United States Patent
Canioni et al.

(10) Patent No.: US 7,609,379 B2
(45) Date of Patent: Oct. 27, 2009

(54) DETECTING LASER-INDUCED FLUORESCENCE EMISSIONS

(75) Inventors: Lionel Canioni, Gradignan (FR); Stéphane Santran, Gradignan (FR); Bruno Bousquet, Gradignan (FR)

(73) Assignee: Centre National de la Recherche Scientifique - CNRS (FR)

( * ) Notice: Subject to any disclaimer, the term of this patent is extended or adjusted under 35 U.S.C. 154(b) by 329 days.

(21) Appl. No.: 11/664,432

(22) PCT Filed: Sep. 30, 2005

(86) PCT No.: PCT/FR2005/002419

§ 371 (c)(1),
(2), (4) Date: Jun. 12, 2007

(87) PCT Pub. No.: WO2006/037879

PCT Pub. Date: Apr. 13, 2006

(65) Prior Publication Data

US 2008/0084562 A1    Apr. 10, 2008

(30) Foreign Application Priority Data

Oct. 1, 2004    (FR) .................................. 04 52235

(51) Int. Cl.
*G01J 3/30*    (2006.01)

(52) U.S. Cl. ..................................... 356/318

(58) Field of Classification Search ......... 356/317–318; 285/12
See application file for complete search history.

(56) References Cited

U.S. PATENT DOCUMENTS

| 5,615,008 | A | 3/1997 | Stachelek |
| 6,673,497 | B2 | 1/2004 | Efimov et al. |
| 6,771,368 | B1 * | 8/2004 | Chadwick ................... 356/318 |
| 7,446,877 | B2 * | 11/2008 | Li et al. ...................... 356/326 |
| 2002/0045104 | A1 | 4/2002 | Efimov et al. |
| 2003/0107732 | A1 | 6/2003 | Sasaki et al. |
| 2003/0234928 | A1 * | 12/2003 | Lucas et al. ................. 356/318 |
| 2004/0169854 | A1 | 9/2004 | Vo-Dinh et al. |
| 2005/0052649 | A1 * | 3/2005 | Tsujita ........................ 356/328 |

FOREIGN PATENT DOCUMENTS

WO    WO 02/095376 A2    11/2002

OTHER PUBLICATIONS

G. Arca et al., "Detection of Environmental Contaminants by Time Resolved Laser Induced Breakdown Spectroscopy Technique," Institute of Electrical & Electronics Engineers, vol. 2, May 28, 1996.
Zahid Yaqoob et al., "High-speed two-dimensional laser scanner based on Bragg gratings stored in photothermorefractive glass," Applied Optics, vol. 42, No. 26, Sep. 10, 2003.

* cited by examiner

*Primary Examiner*—Kara E Geisel
(74) *Attorney, Agent, or Firm*—DLA Piper LLP (US)

(57) ABSTRACT

A system for detecting a chemical element within a material including at least one laser emission means for ionizing part of the material to generate fluorescence; at least one transmitting Bragg grating that filters the wavelength corresponding to the deexcitation wavelength of the element; and at least one photodiode that detects a line corresponding to the filtering wavelength, wherein the at least one Bragg grating is mobile to vary the filtering wavelength.

10 Claims, 4 Drawing Sheets

DETECTING LASER-INDUCED FLUORESCENCE EMISSIONS

RELATED APPLICATION

This is a §371 of International Application No. PCT/FR2005/002419, with an international filing date of Sep. 30, 2005 (WO 2006/037879 A1, published Apr. 13, 2006), which is based on French Patent Application No. 04/52235, filed Oct. 1, 2004.

TECHNICAL FIELD

The technology herein relates to tools for determining a sample chemical composition, more particularly, to detecting chemical elements in a sample by laser-induced fluorescence (LIF) emissions.

BACKGROUND

For approximately ten years, a large number of applications have a sample analysis requirement, whether in solid, liquid or gaseous form. Laboratories have developed a number of diagnostics tools allowing the composition of a sample to be determined to meet these requirements. The tools may use various chemical, physical, or even mechanical principles. They include, for example, the methods of plasma emission spectroscopy (ICP), spectrometry, electrochemistry, calorimetry, etc.

A large number of analyses are based on gas chromatography combined with known mass spectroscopy or plasma emission spectroscopy techniques. In spite of the efficiency of analysis tools in terms of detection threshold, the latter are, on one hand, very expensive and, on the other hand, not portable. They are installed in analysis laboratories, require very careful preparation of the sample, and need highly qualified staff to carry out the measurements and interpret the spectra. One analysis thus requires, on average, a period of three days between collection of samples and determining the result of its composition.

While using those diagnostics tools, the LIBS (Laser Induced Breakdown Spectroscopy) technology, invented in laboratories in 1989, has become over the last few years a means of analysis of the atomic composition of materials competing with the ICP. The LIBS may have the advantage of portability and lesser preparation of the sample. This allows the analyses to be carried out on site. The well known general principle of the LIBS technology is to analyze fluorescence emitted by the previously atomized sample. The analysis of ratios of emission lines allows a quantitative measurement of the concentration of the species in the material.

More specifically, a material, whether it is in solid, liquid or gaseous form may, after excitation by a laser, be transformed into plasma (mixture of free electrons, ions, atoms and molecules) resulting from the ionization, for example, by multiphotonic absorptions or by the tunnel effect. If excitation of the material is significant enough, other well known physical phenomena come into play such as cascade ionizations and collisions between free electrons. The effects increase the temperature of the plasma produced. The Bremsstrahlung of the moving electrons (inverse Bremsstrahlung effect) therefore gives a white light emitted by the plasma. Analysis of the radiative deexcitation of the atoms and ions therefore allows the latter to be traced back to the composition via a spectral analysis of the white light emitted by the plasma. The atomic lines having a much longer lifetime than the continuum of white light, a delayed detection of the spectrum allows the atomic lines of the spectrum to be isolated for tracing back to the composition.

Conventional laser sources used in that type of application are nanosecond YAG type laser sources with a 1,064 nm wavelength generating energy pulses on the order of a few tens of millijoules. Focusing the laser beam is carried out with the aid of a lens generally protected by an interchangeable protection window.

The detection and collection of the fluorescence are carried out according to known techniques with an optical fiber placed at the level of the plume of the plasma. The light transmitted by the fiber is sent into a spectrometer for detection by a CCD or ICCD camera accompanied by a full-size grating or more generally a monochromator. Recognition of the LIBS spectra requiring a good optical resolution (typically between 1,000 and 3,000), to be able to differentiate samples of similar composition on a broad spectrum, the existing systems use the following detection methods: a spectrometer equipped with a full-size grating with variable blaze, or a set of spectrometers in parallel, or a spectrometer equipped with a full-size grating and a prism.

The disadvantages of such detection systems are their cost, and low luminosity linked to the entrance slit making exploitation of the results difficult.

Known waveguide integrated spectrometers include U.S. Pat. No. 5,615,008. Such a system includes a waveguide inside of which Bragg gratings are placed to redirect the light from the waveguide outwardly of the guide. Such a system can operate as a spectrophotometer, spectrofluorimeter, or other means for analyzing the components of lights after the passage of a sample.

Once again, the luminosity and the resolution obtained by the type of spectrometer are not sufficient for certain element detection applications. The Bragg gratings inscribed to reflect the light outside of the fiber are not very effective due to the low thickness of the grating inscribed limited by the diameter of the optical fiber.

Moreover, the fact that the Bragg gratings are directly integrated into the optical fiber prevents the detection wavelengths of the gratings from being tuned because the angle of incidence on the Bragg grating of the guided light is fixed. The gratings inscribed in the fibers therefore have a number of practical limitations.

It could therefore be advantageous to provide a detection system which is wavelength tunable. It could also be advantageous to provide an element detection system allowing a compact system to be obtained, while maintaining good resolution and a large degree of luminosity.

SUMMARY

We provide a system for detecting a chemical element within a material including at least one laser emission means for ionizing part of the material to generate fluorescence, at least one transmitting Bragg grating that filters the wavelength corresponding to the deexcitation wavelength of the element, and at least one photodiode that detects a line corresponding to the filtering wavelength, wherein the at least one Bragg grating is mobile to vary the filtering wavelength.

BRIEF DESCRIPTION OF THE DRAWINGS

Our technology will be better understood with the aid of the description, made hereafter purely by way of explanation, of selected aspects, referring to the figures appended where.

DETAILED DESCRIPTION

Figure 1:
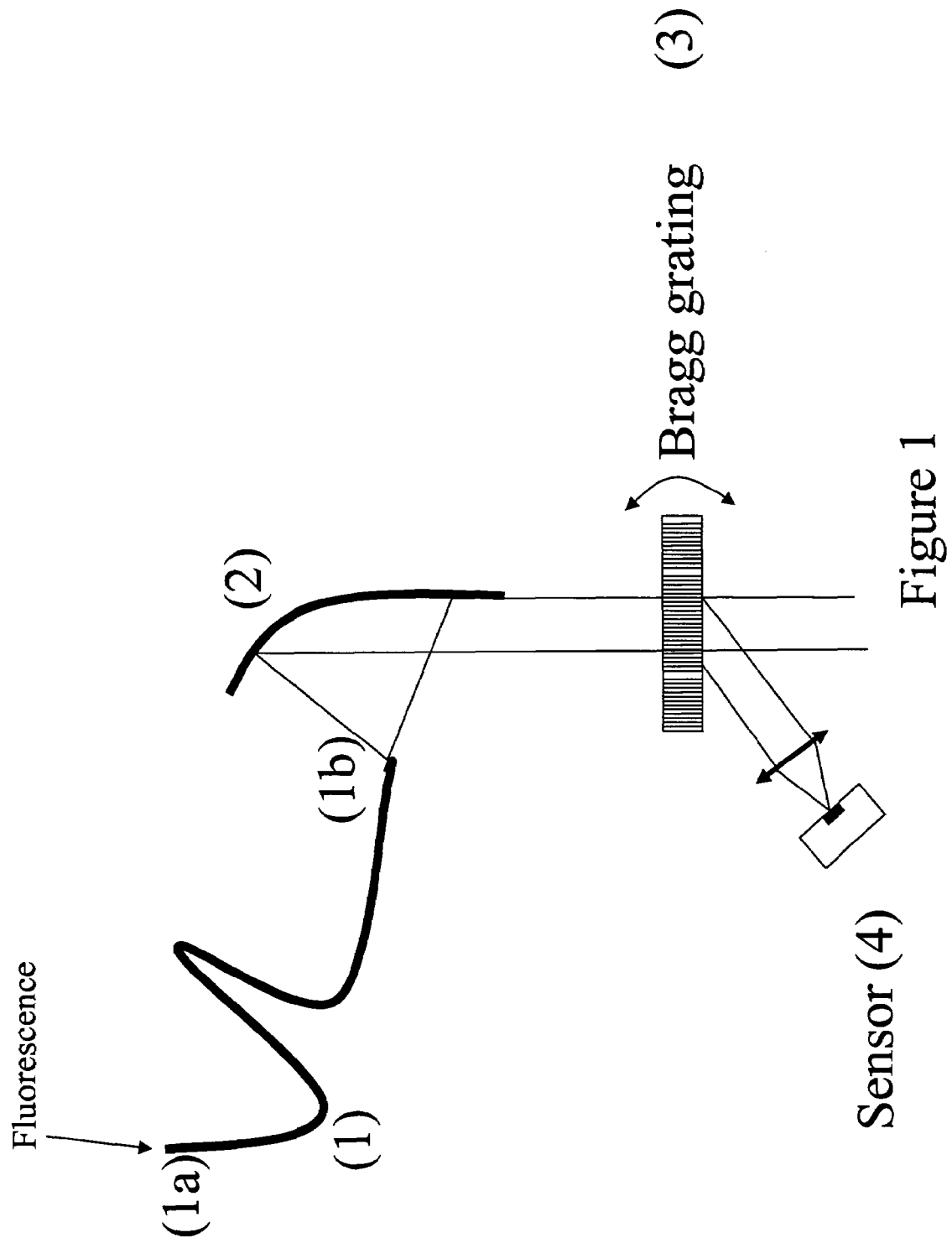
FIG. 1 is a schematic view of a collection and detection system in single-sensor mode.

It will be appreciated that the following description is intended to refer to specific examples of structure selected for illustration in the drawings and is not intended to define or limit the disclosure, other than in the appended claims.

In the field of detecting wavelengths, highly effective Bragg gratings are known, for example, U.S. Pat. No. 6,673,497, where an accurate analysis of the results from the grating is presented.

The very high efficiency of the gratings allows, for example, a compact detection device to be designed, that may be used in a laser-induced fluorescence emission detection system, for example, by an LIBS technique.

Our technology concerns systems for detecting chemical elements within a material comprising at least one laser emission for ionizing one part of the material to generate fluorescence, at least one transmitting Bragg grating that filters the wavelength corresponding to a deexcitation wavelength of the element of at least one photodiode for detecting the line corresponding to the filtering wavelength, wherein the at least one Bragg grating is mobile to vary the filtering wavelength.

The specific use of a mobile Bragg grating to vary the filtering wavelength allows a wavelength tunability to be obtained. In that way, it is, for example, possible to cover a broad wavelength spectrum and, therefore, allow a plurality of chemical elements to be detected.

Turning to FIG. 1, one exemplary system includes an optical fiber (1) that transports light derived from the plasma. The system may therefore be used with a material placed at the level of the beginning of the optical fiber (1a). The laser emission at the level of the material creating the plasma at the level of one end of the optical fiber risks damaging the latter via projections. Therefore, a quartz plate is possibly used to protect the end of the optical fiber (1).

Fluorescence is therefore transmitted up to the final end (1b) of the optical fiber (1). The end of the optical fiber (1b) is placed at a focal point of an off-axis paraboloidal mirror (2). The light is therefore reflected and collimated as illustrated in FIG. 1. The Bragg grating (3) is a volume transmitting Bragg grating. The grating may be of the type in U.S. Pat. No. 6,673,497, for example, more specifically used as wavelength selector as in FIG. 11a of the aforementioned patent. They are, for example, fabricated in a Photo Thermo Refractive (PTR) material and their engraving is carried out with the aid of a UV laser exposure and a thermal development. A known property of the gratings is that they only become one single wavelength with a very high efficiency, for example, greater than 95%, whereas the other wavelengths are transmitted without diffraction. The wavelength is therefore sent to the sensors (4) to detect the lines corresponding to the element sought.

Typical dimensions and characteristics for producing the device are now provided. It is understood that the dimensions are not at all restrictive and must not limit the scope of the appended claims.

The grating has a characteristic dimension of 2.5 cm, for a beam of approximately 2 cm of aperture. The paraboloidal mirror has a characteristic dimension of approximately 5 cm, and the output end of the fiber is placed at the level of the focal point of the parabola. The optical fibers have a core dimension of approximately 100 μm. Finally, the typical distances between the main elements of the device are:

between the paraboloidal mirror and the grating: 5 cm,
between the end of the fiber and the mirror: 5 cm.

The gratings are adapted in terms of pitch, blaze, and profile of the index gradient according to the wavelength sought, the acceptable resolution and the element considered. Such developments are known in the field of diffraction gratings.

Once the wave is diffracted by the Bragg grating, the latter is focused by a lens and detected by a diode. The type of diode is particularly suitable for fluorescence emissions, for example, in LIBS techniques.

Indeed, as pointed out above, fluorescence emission is accompanied with the emission of a white light emitted by the plasma and produced by various phenomena, including the inverse Bremsstrahlung effect. In addition, the atomic lines having a much longer lifetime than the continuum of white light, a delayed detection of the spectrum allows the atomic lines of the spectrum to be isolated for referring back to the composition.

The photodiodes used are therefore, for example, avalanche photodiodes that may be synchronized with respect to the laser shot. Thus, activation of the photodiodes may be delayed so as not to capture the continuum of white light.

The typical size of the detectors is approximately 1 $mm^2$.

Figure 2:
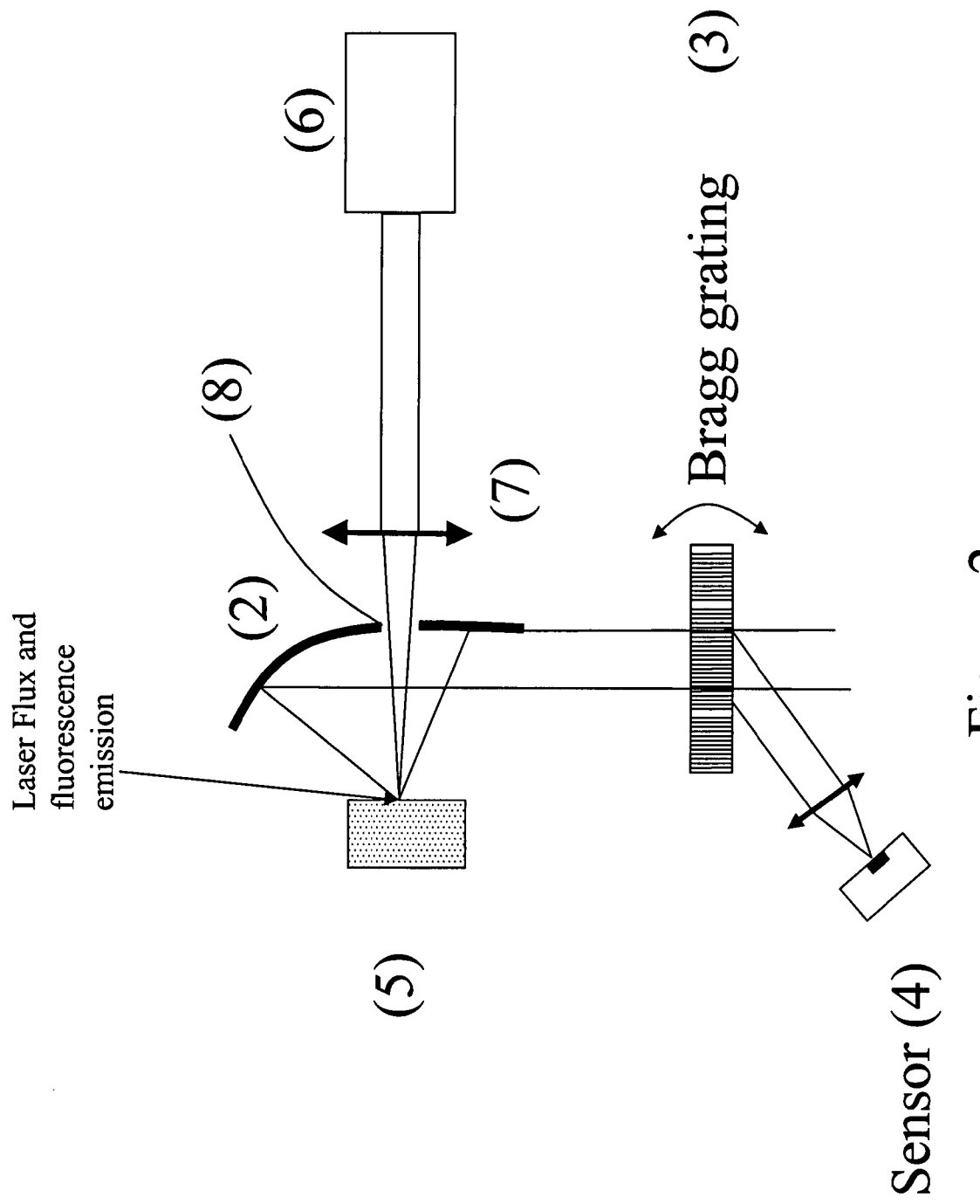
FIG. 2 is another schematic of a collection and detection system.

Another system, illustrated in FIG. 2, is now described where the fluorescence is emitted directly at the level of the focal point of the paraboloidal mirror (2). The laser (6) is focused on the material (5) containing the elements to be detected with the aid of a lens (7) via a hole (8) produced in the fluorescence collecting parabola (2).

It will be noted that the optical fiber (2) is no longer required. The detection principles are therefore the same as in the system shown in FIG. 1. The luminosity of the system may even be increased by minimising the optical trajectory.

Figure 3:
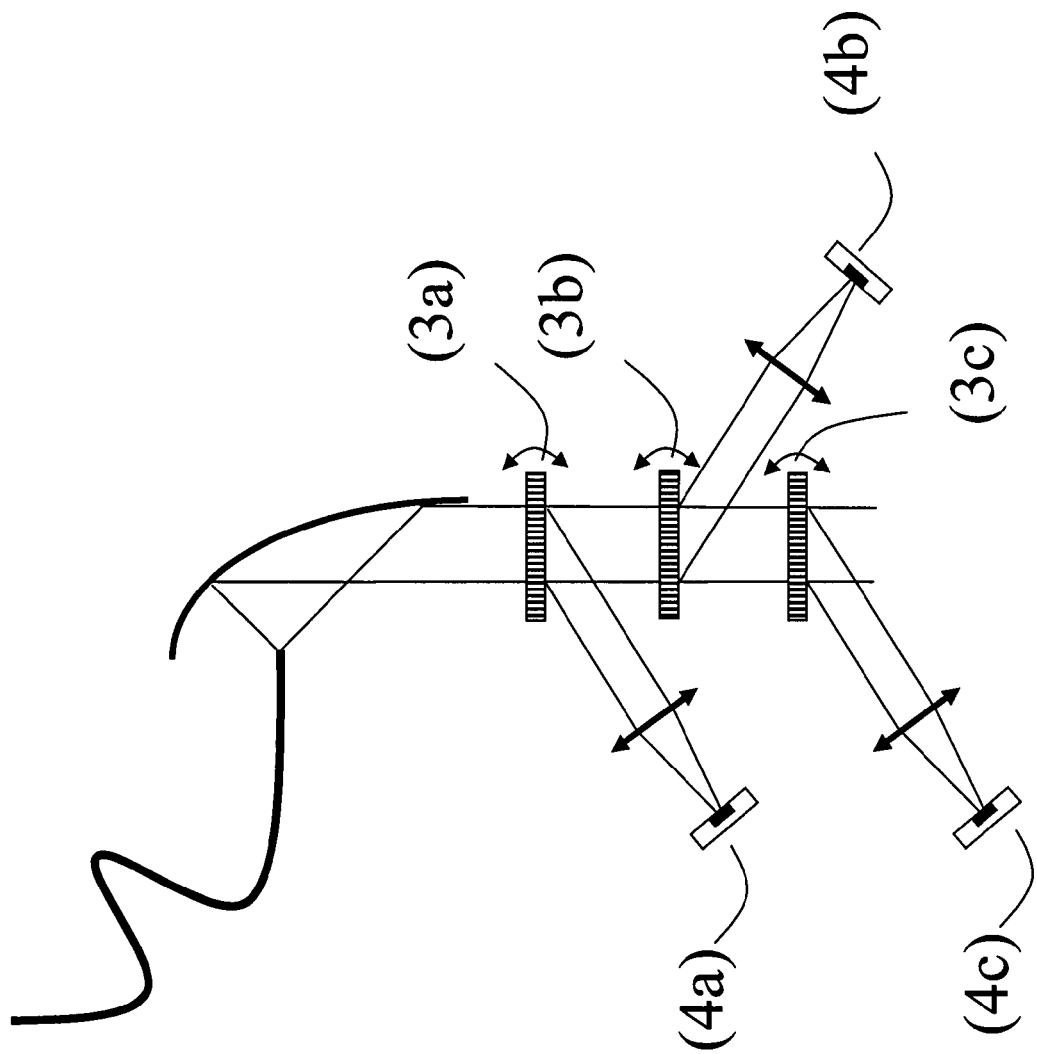
FIG. 3 is a schematic view of a collection and detection system in multi-sensor mode.

Illustrated in FIG. 3, the system may also comprise a combination of a plurality of gratings to detect a plurality of atomic lines. To make the system adjustable, the rotation of one grating with respect to an incident ray allows a variable wavelength to be transmitted on a certain range of wavelengths.

By increasing the number of gratings, on one hand, a plurality of chemical elements may be detected, and on the other hand, more of the spectrum may be covered by rotation of the gratings. It may be noted that with four Bragg gratings, the entire visible spectrum may be covered.

Thus, an incident ray (10) arrives on a first grating (3a). The wavelength corresponding to the Bragg grating length $\lambda_0$ is therefore deviated according to the ray (10a), whereas the other wavelengths continue their trajectory according to the ray (10b).

The possible stacking of a plurality of gratings (3a), (3b) and (3c) therefore allows a plurality of lines to be detected according to the wavelengths selected by the gratings. The lines are detected by the photodiodes (4a), (4b), (4c).

Detection of a particular line is also facilitated by the rotation of a grating. Indeed, if the wavelength sought is, for example $\lambda_1$ and the grating installed has a Bragg wavelength $\lambda_0$, then rotation of the grating modifies the angle of incidence of the ray and thus the wavelength transmitted ($\lambda_0$ depending on the angle of incidence). Between the grating and the detector, a sufficiently wide lens is therefore used to focus the diffracted light on the detector.

Figure 4:
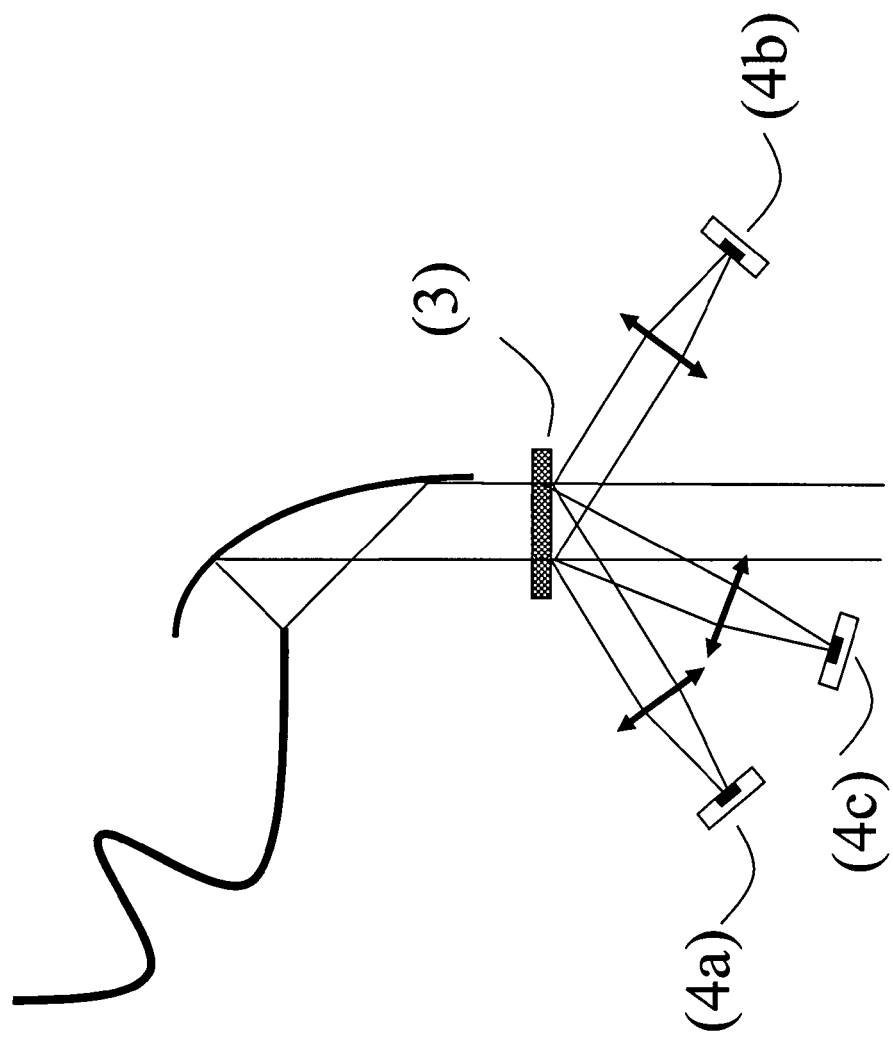
FIG. 4 shows one multi-sensor aspect with a Bragg grating wherein a plurality of diffraction gratings are engraved into the latter.

Illustrated in FIG. 4, the system may also comprise a Bragg grating wherein a plurality of diffraction gratings are engraved inside the latter. In that case, the various wavelengths chosen are diffracted according to various directions towards the photodiodes 4a 4b, 4c. This allows a more compact spectrometer equivalent to that of FIG. 3.

Although the apparatus and methods have been described in connection with specific forms thereof, it will be appreciated that a wide variety of equivalents may be substituted for the specified elements described herein without departing from the spirit and scope of this disclosure as described in the appended claims.

The invention claimed is:

1. A system for detecting a chemical element within a material comprising:
- at least one laser emission means for ionizing part of the material to generate fluorescence;
- at least one transmitting Bragg grating that filters the wavelength corresponding to the deexcitation wavelength of the element; and
- at least one photodiode that detects a line corresponding to the filtering wavelength, wherein the at least one Bragg grating is mobile to vary the filtering wavelength.

2. The system according to claim 1, wherein the photodiode is synchronizable with emissions from the laser.

3. The system according to claim 1, wherein the photodiode is activated with a delay with respect to the emission from the laser.

4. The system according to claim 2, wherein the photodiode is activated with a delay with respect to the emission from the laser.

5. The system according to claim 1, wherein the photodiode is an avalanche photodiode.

6. The system according to claim 1, further comprising a lens for focusing rays emitted by the Bragg grating towards the photodiode.

7. The system according to claim 1, further comprising a collimation mirror for collimating the fluorescence towards the Bragg grating.

8. The system according to claim 7, further comprising at least one optical fiber for transporting the fluorescence.

9. The system according to claim 8, wherein one end of the optical fiber corresponds to a focal point of the collimation mirror.

10. The system according to claim 7, wherein material is placed at a level of the focal point of the collimation mirror.

* * * * *